United States Patent [19]

Tsukaya et al.

[11] Patent Number: 4,503,841
[45] Date of Patent: Mar. 12, 1985

[54] ENDOSCOPE SYSTEM

[75] Inventors: Takashi Tsukaya, Tokyo, Japan; Takeshi Takamatsu, deceased, late of Hachioji, Japan, by Tokuyuki Takamatsu, legal representative

[73] Assignee: Olympus Optical Co., Ltd., Tokyo, Japan

[21] Appl. No.: 435,755

[22] Filed: Oct. 21, 1982

[30] Foreign Application Priority Data

Oct. 22, 1981 [JP] Japan ................................ 56-168947

[51] Int. Cl.³ .............................................. A61B 1/00
[52] U.S. Cl. ......................................... 128/4; 604/67; 137/624.11
[58] Field of Search ....................... 128/4–8, 128/748; 222/14, 63, 639; 137/624.11, 635; 604/50, 31, 65, 67, 245

[56] References Cited

U.S. PATENT DOCUMENTS

| 3,869,067 | 3/1975 | Ashmead et al. | 222/639 |
| 4,200,911 | 4/1980 | Matsumato | 137/624.11 |
| 4,343,300 | 8/1982 | Hattori | 128/6 |
| 4,402,310 | 9/1983 | Kimura | 128/6 |

FOREIGN PATENT DOCUMENTS

| 26497 | 4/1981 | European Pat. Off. | |
| 1791280 | 7/1974 | Fed. Rep. of Germany | 128/4 |
| 2949827 | 6/1981 | Fed. Rep. of Germany | |

Primary Examiner—Edward M. Coven
Assistant Examiner—Max F. Hindenburg

[57] ABSTRACT

An endoscope system is provided with a pump for feeding air into a body cavity through an endoscope, and a pump driving circuit for adjusting current to be supplied to the pump. Control data for controlling the pump is stored in an ROM. While the ROM is held in an enabling state by a chip selector according to setting data from switches and a zerocross detector, the control data is read out from the ROM by a CPU, and the pump is driven in accordance with the control data. If the ROM is not in the enabling state although the CPU is fetching the setting data and control data, then an alarm signal is delivered from a NOR gate, and the pump is driven so as to provide a maximum quantity of air supply.

5 Claims, 24 Drawing Figures

ENDOSCOPE SYSTEM

BACKGROUND OF THE INVENTION

This invention relates to an endoscope system, more specifically to an endoscope system provided with a safety circuit.

Recently, microcomputers have come to be applied to uses in a wide variety of apparatus and systems including endoscope systems. Application of a microcomputer to the use in an endoscope system requires at least the minimum of a safe measure to counter run over of a CPU of the microcomputer due to noise or heat, since the endoscope of the system is used for diagnosis on the human body or the like. Especially in those endoscopes which include air and water supply units or a light source unit, if the CPU runs over, air and water supply will be rendered unstable, or illumination light will fail to be supplied to the affected region to be examined. Thus, the affected region cannot be observed through the eyepiece section of the endoscope. This would be a serious situation from a viewpoint of security.

SUMMARY OF THE INVENTION

The object of this invention is to provide an endoscope system with a CPU ensuring at least the minimum of safety even in case of wrong operation of the CPU. "According to the invention, the endoscope has a pump, a memory, a chip selector holding the memory in an enabling state in which control data can be read out from the memory, and a processor fetching setting signals as instruction commands operating the chip selector. The pump is driven in accordance with the control data and an alarm signal is produced when the memory is not maintained in the enabling state even though the setting signals are produced. Upon production of the alarm signal the pump is driven at a fixed rate."

DETAILED DESCRIPTION OF THE PREFERRED EMBODIMENT

Figure 1:
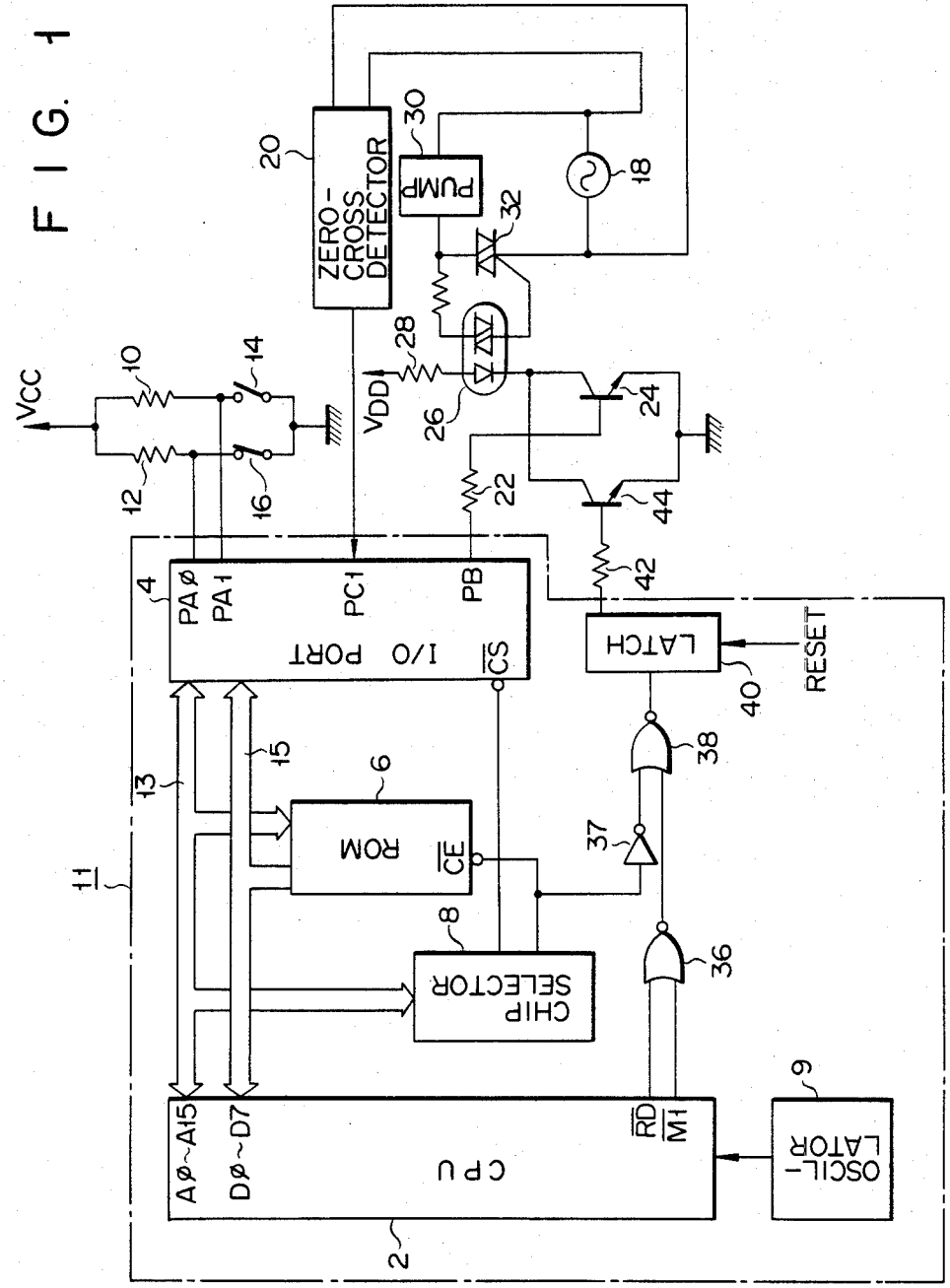
FIG. 1 is a block diagram showing an endoscope system with a CPU according to one embodiment of this invention.

As shown in FIG. 1, a microcomputer 11 is disposed in a light source unit (not shown). The microcomputer 11 comprises a CPU 2, an I/O port 4, an ROM 6, a chip selector 8, and an oscillator 9. Address terminals A$\phi$ to A15 of the CPU 2 are connected to the I/O port 4, the ROM 6, and the chip selector 8 through an address bus 13 so that address data are supplied from the CPU 2 to the individual devices. Data terminals D$\phi$ to D7 of the CPU 2 are connected to the I/O port 4 and the ROM 6 through a data bus 15. Thus, data are read out from the ROM 6 and transmitted to the CPU 2, and data are transferred between the I/O port 4 and the CPU 2.

In a specific circuit arrangement, Z80 (by Zilog Co.) is used for the CPU 2; 8255A (Programmable I/O by Intel Corp.) for the I/O port 4; 2764 (by Intel Corp.) for the ROM 6; and SN74LS138 (by Texas Instrument Co.) for the chip selector 8. These devices are mounted on an IC substrate.

Input terminals PA$\phi$ and PA1 of the I/O port 4 are connected to nodes between pump output setting switches 14 and 16 and resistors 10 and 12, respectively. The resistors 10 and 12 are connected between a power source $V_{CC}$ and the ground. An input terminal PC1 of the I/O port 4 is connected with a zerocross detector 20 for detecting the zerocross point of AC voltage which is supplied from a commercial AC power source 18. The output terminal PB of the I/O port 4 from which a pump driving signal is delivered is connected to the base of a first transistor 24 through a resistor 22. The emitter of the transistor 24 is grounded, and its collector is connected to a power source $V_{DD}$ through the photodiode of a photocoupler 26 and a resistor 28. The commercial AC power source 18 is connected to a pump 30 through a Triac 32 for phase-controlling power supplied to the pump 30. A resistor 34 and the Triac of the photocoupler 26 are connected between the gate of the Triac 32 and a node between the Triac 32 and the pump 30 so that the Triac 32 is ignited at regular intervals.

The chip selector 8 is connected to the chip selecting terminal $\overline{CS}$ of the I/O port 4 and the chip enabling terminal $\overline{CE}$ of the ROM 6, and the CPU 2 selects a chip in accordance with an instruction code. The memory readout signal terminal $\overline{RD}$ and machine cycle signal terminal $\overline{M1}$ of the CPU 2 are connected to an OR gate 36. The output of the OR gate 36 and the output of an inverter 37 connected to a chip enabling signal line are connected to a NOR gate 38, whose output is connected to a latch 40. The output of the latch 40 is connected to the base of a second transistor 44 through a resistor 42. The collector and emitter of the second transistor 44 are connected between the photodiode of the photocoupler 26 and the ground.

Figure 2:
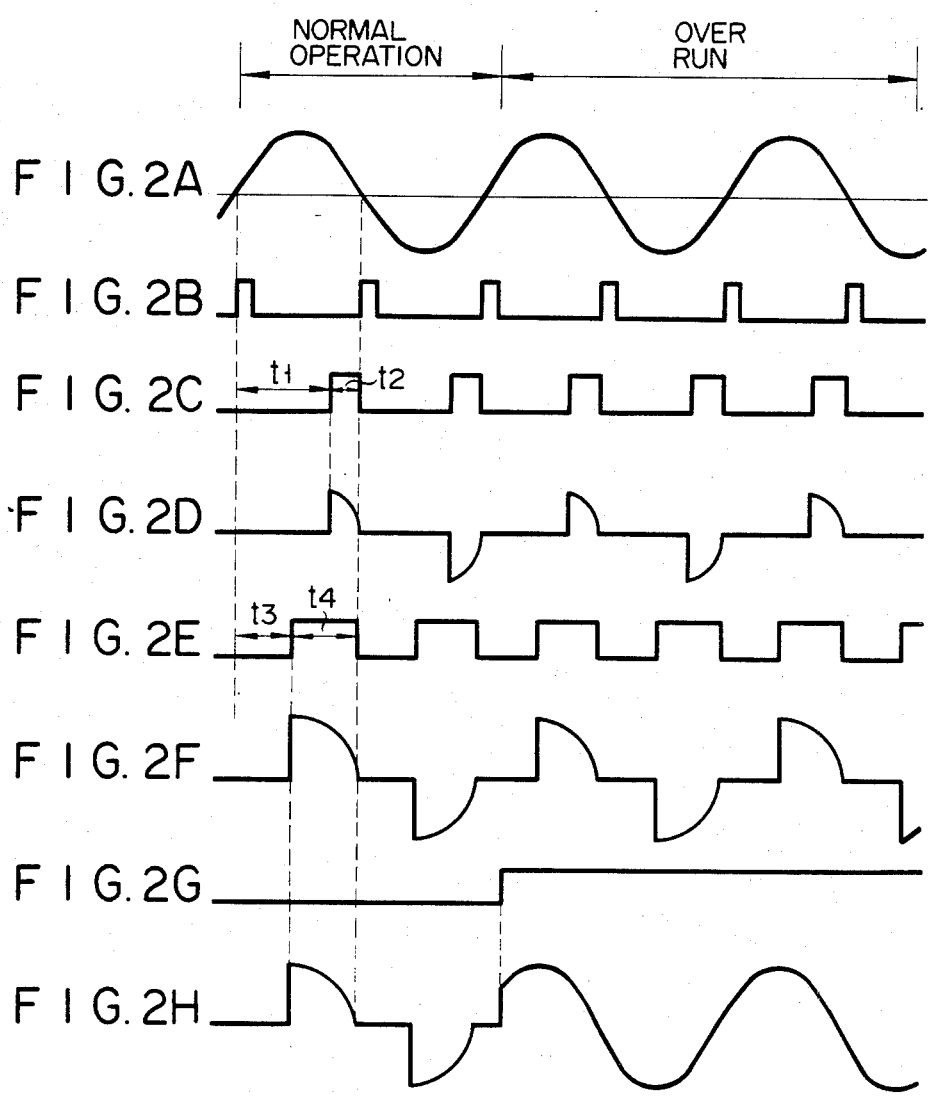
FIGS. 2A to 2H show a timing chart for illustrating the operation of the endoscope shown in FIG. 1.

Constructed in this manner, the one embodiment of this invention operates as follows. When commercial AC supply voltage is supplied to the zerocross detector 20, as shown in FIG. 2A, the zerocross detector 20 detects the zerocross point, and produces a zerocross signal as shown in FIG. 2B. The produced zerocross signal is applied as an instruction code to the input terminal PC1 of the I/O port 4. Thereupon, when the pump output setting switch 16 is closed, a low level signal is supplied as an instruction code to the input terminal PA$\phi$ of the I/O port 4. The low level signaland the zerocross signal are fetched as instruction codes to the CPU 2 through the data bus 15. In response to a fetched instruction code for pump control, the CPU 2 causes the chip selector 8 to select the ROM 6 in which data for pump control is stored and the I/O port 4 for pump control. Thus, in response to an instruction code, prescribed data, i.e., data for a delay time t1, is read out from the ROM 6 with a prescribed address. The data read out in this manner is transferred from the ROM 6 to the selected I/O port 4. As a result, a low level signal is delivered from the output terminal PB of the I/O port 4 for the delay time t1 starting from a zerocross point, as shown in FIG. 2C, and then a high level signal is delivered for a time t2 directly following the time t1 and ending at the next zerocross point. Accordingly, the first transistor 24 is off for th delay time t1 and is on for the time t2. During the time t2 when the first transistor 24 is one, the photodiode of the photocoupler 26 emits light, and the photo-Triac of the photocoupler 26 is turned on to turn on the Triac 32. As a result, the pump 30 is supplied with power from the AC power source 18 for the time t2. Thus, a current as shown in FIG. 2D is continuously supplied to the pump 30 to secure a proper quantity of air supply, etc.

If the pump output setting switch 14 is closed instead of the switch 16, a delay time t3 is read out in place of the delay time t1, and an output signal as shown in FIG. 2E is delivered from the output terminal PB of the I/O port 4. Thus, a current as shown in FIG. 2F is supplied to the pump 30 to secure a modified proper quantity of air supply.

The CPU 2 can decide whether the frequency of the AC power source is 50 Hz or 60 Hz by counting zero-cross signals as shown in FIG. 2B. A proper delay time is selected from data in the ROM 6 on the basis of the decision. Thus, whether the frequency is 50 Hz or 60 Hz, a specified quantity of air supply can be secured by the pump 30.

Figure 3:
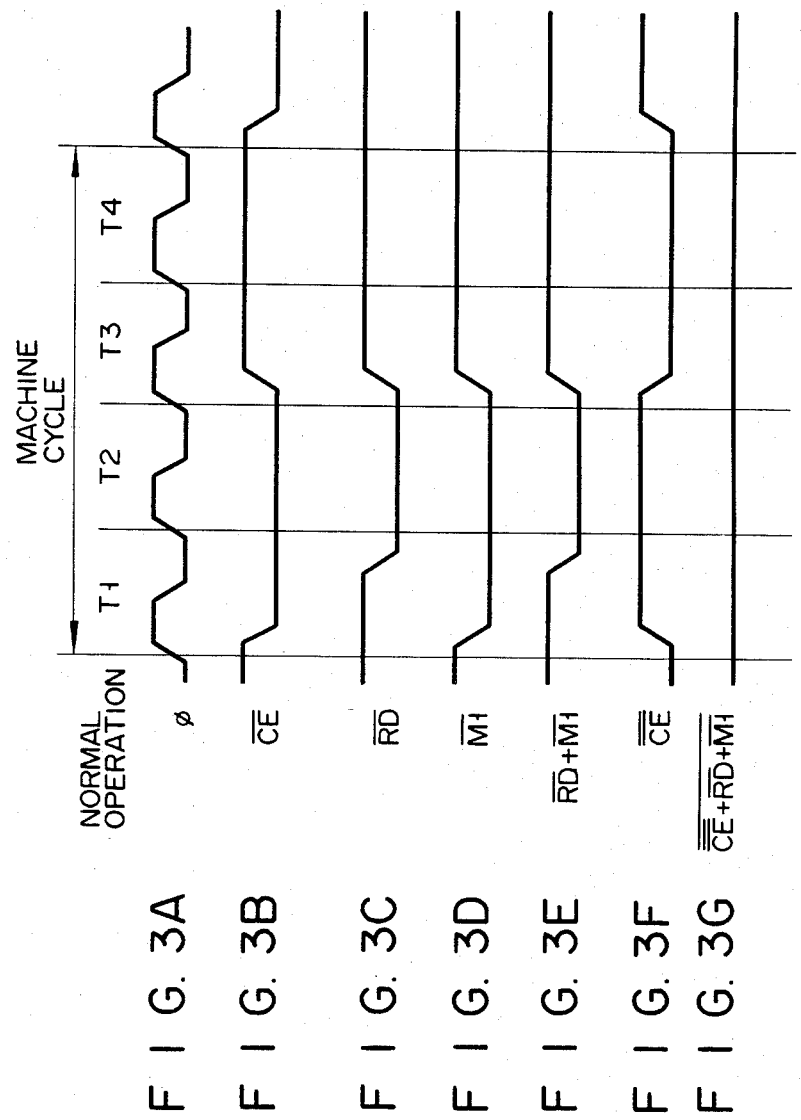
FIGS. 3A to 3G show a timing chart of a microcomputer in the endoscope system of FIG. 1 obtained when the microcomputer operates normally.

Referring now to FIGS. 3A to 3G and 4A to 4G, there will be described timings of the CPU 2 for cases where the CPU 2 operates normally and where it runs over due to noise or heat. FIGS. 3A to 3G show timings in a machine cycle to fetch instruction codes. The CPU 2 is supplied with clock pulses as shown in FIG. 3A from the oscillator 10. A chip selecting signal is applied from the chip selector 8 to the chip selecting terminal $\overline{CS}$ of the I/O port 4. If the chip selecting signal goes low, the I/O port 4 is selected, and the I/O gate of the I/O port 4 is opened. Accordingly, an instruction code is fetched from the I/O port 4 to the CPU 2 through the data bus 13. A chip selecting signal as shown in FIG. 3B is applied from the chip selector 8 to the chip enabling terminal $\overline{CE}$ of the ROM 6. If this chip selecting signal goes low, the ROM 6 is selected and held ready for readout. Accordingly, the instruction code is fetched from the ROM 6 to the CPU 2 with a prescribed address. At this time, the memory readout terminal $\overline{RD}$ is maintained at low level, as shown in FIG. 3C. When the instruction code is fetched to the CPU 2, the machine cycle signal terminal $\overline{M1}$ is also maintained at low level, as shown in FIG. 3B. Therefore, while the output of the OR gate 36 is at low level, as shown in FIG. 3E, the CPU 2 reads instructions. Meanwhile, if the chip enabling terminal $\overline{CE}$ of the ROM 6 is at low level, data is read from the ROM 6. Thus, the output of the inverter 37 is as shown in FIG. 3F. As the outputs of the inverter 37 and the OR gate 36 are supplied to the NOR gate 38, the output of the NOR gate 38 is maintained at low level, as shown in FIG. 3G, and the second transistor 44 is kept off. In this state, current supply to the pump 30 is controlled in accordance with the on-off operation of the first transistor 24.

Figure 4:
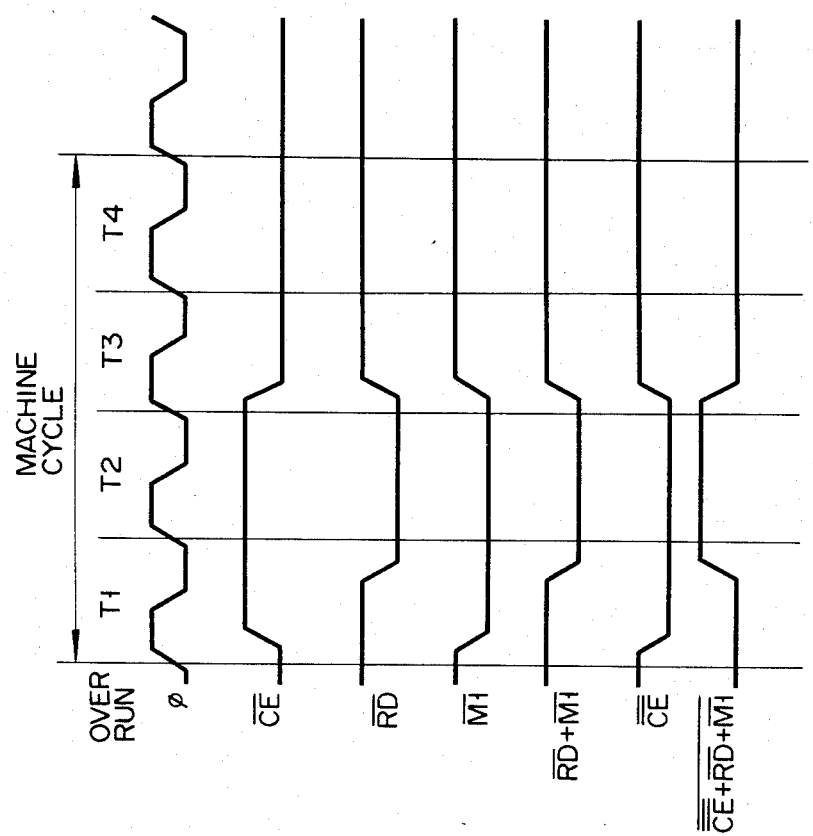
FIGS. 4A to 4G show a timing chart of the microcomputer obtained when the microcomputer runs over.

If the CPU 2 runs over, then the CPU 2 will fetch instruction data from some other memory region than the ROM 6. Namely, the chip selector 8 selects an empty region (e.g., a spare region for an additional ROM) on the IC mounting base on which some other chip than the ROM 6 is to be mounted, and instruction data is fetched from the empty region to the CPU 2. In other words, a high level non-enabling signal as shown in FIG. 4B is applied to the chip enabling terminal $\overline{CE}$ of the ROM 6, and instruction data is fetched to the CPU 2 also in a period during which the ROM 6 is not selected. Thus, the terminals $\overline{RD}$ and $\overline{M1}$ of the CPU 2 are maintained at low level, as shown in FIGS. 4C and 4D. Accordingly, the outputs of the inverter 37 and the OR gate 36 are kept at low level, as shown in FIGS. 4F and 4E, respectively, and a high level signal is delivered from the NOR gate 38, as shown in FIG. 4G. This high level signal is latched in the latch 40. As a result, a signal as shown in FIG. 2G is applied to the second transistor 44 to turn on the same. Thus, the Triac 32 is maintained in conduction, and the pump 30 is supplied with an AC current which is not phase-controlled, as shown in FIG. 2H, so that the maximum quantity of air supply is obtained. When an operator notices the over run of the microcomputer, he is to stop the operation of the system after suspending endoscopic diagnosis or treatment. At this time, if the operator depresses a reset button, a reset signal is applied to the latch 40 to clear the same.

In the aforementioned embodiment, an AC current is supplied directly to the pump 30 while the second transistor 44 is on. Alternatively, however, a phase-controlled AC current may be applied to the pump 30 so as to set a limited quantity of air supply.

According to the embodiment mentioned above, even if the CPU runs over, the pump can be securely driven to ensure stable air supply. Thus, the endoscope system can be improved in safety.

Figure 5:
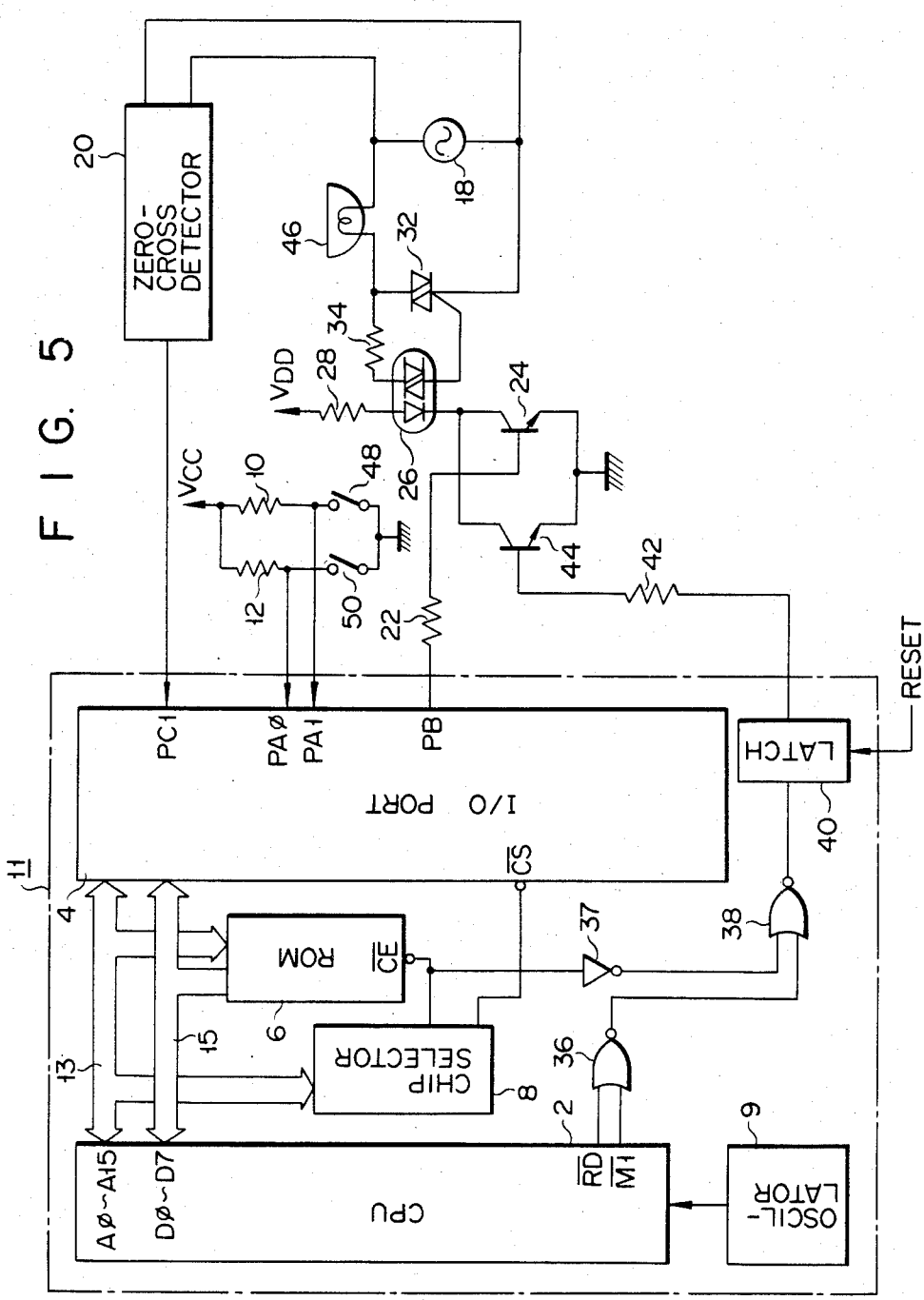
FIG. 5 is a schematic view showing an endoscope system according to another embodiment of the invention.

Referring now to FIG. 5, another embodiment of this invention will be described in detail. In FIG. 5, like reference numerals are used to designate the same portions as shown in FIG. 1. In the embodiment of FIG. 5, an AC current supplied to a light source 46 for the endoscope, instead of the pump 30, is phase-controlled by a Triac 32. The pump output setting switches 14 and 16 are replaced with light intensity setting switches 48 and 50. If one of the switches 48 and 50 is selected and closed, a CPU 2 reads necessary data, sets a delay time corresponding to a given zerocross signal, and causes a signal as shown in FIG. 2C to be delivered from the output terminal PB of an I/O port 4. In the aforementioned manner, therefore, the AC current as shown in FIG. 2F is supplied to the light source 46 to make it glow with prescribed brightness. When the switches 48 and 50 are shifted, the delay time and the brightness of the light source 46 are changed.

Thereupon, when instruction data is fetched to the CPU 2 in the normal state, the signal applied to the chip enabling terminal $\overline{CE}$ of an ROM 6 is kept at low level, and the output terminals $\overline{RD}$ and $\overline{M1}$ of the CPU 2, as well as the output of a NOR gate 38, are kept at low level. If the CPU 2 runs over, the signal applied to the chip enabling terminal $\overline{CE}$ of the ROM 6 in the aforesaid state goes high, so that the output of the NOR gate 38 goes high, and is latched in a latch 40. Accordingly, a second transistor 44 is turned on, the Triac 32 continues to conduct, and the light source 46 glows with maximum brightness. Thus, the visual field in the eyepiece section of the endoscope is secured.

Also in this embodiment, the light source 46 may be so designed as to glow not with maximum brightness but wil limited brightness.

According to the aforementioned embodiment, the light source for the endoscope continues to glow even if the CPU runs over, so that the safety of the endoscope system may be maintained.

What we claim is:
1. An endoscope system comprising:
a memory for storing control data;

a chip selector operatively connected to said memory for applying a chip enabling signal to the memory to hold the memory in an enabling state in which the control data can be read out from the memory;

means for producing setting signals;

a processor operatively connected to said means for fetching the setting signals as instruction commands, operating the chip selector and reading out the control data from the memory in accordance with the setting signals when the memory is maintained in the enabling state by the chip selector;

a pump in said endoscope system for supplying fluid to a body cavity;

means operatively connected to the pump for adjusting power supplied to the pump in accordance with the control data;

means for producing an alarm signal while the memory is not maintained in the enabling state by the chip selector which is operated under the control of the processor although the setting signals are being produced; and means operatively connected to said alarm signal producing means for causing the adjusting means to drive the pump at a fixed rate in response to the alarm signal.

2. An endoscope system according to claim 1, wherein said processor has a first terminal from whih a first logic signal is delivered while the instruction commands are fetched, and a second terminal from which a second logic signal is delivered while the control data is read out from the memory, and the alarm signal producing means produces the alarm signal when the processor does not erroneously cause the chip selector to maintain the memory in the enabling state although the first and second logic signals are being produced.

3. The endoscope system according to claim 1, wherein said means for producing the setting signals includes means for discriminating power supply frequency and a switching circuit.

4. The endoscope system according to claim 1, wherein said means for producing the alarm signal includes a logic circuit including a latch circuit for latching the alarm signal.

5. The endoscope system according to claim 1, wherein said means for causing the pump adjusting means to drive the pump includes a switching element to be closed in response to the alarm signal.

* * * * *